United States Patent [19]
Sabahi et al.

[11] Patent Number: 5,347,043
[45] Date of Patent: Sep. 13, 1994

[54] PROCESS FOR PREPARING MICHAEL ADDITION PRODUCTS

[75] Inventors: Mahmood Sabahi, Baton Rouge; Robert G. Irwin, Prairieville, both of La.

[73] Assignee: Albemarle Corporation, Richmond, Va.

[21] Appl. No.: 169,261

[22] Filed: Dec. 20, 1993

[51] Int. Cl.$^5$ .................. C07C 69/34; C07C 69/38; C07C 67/465; C07C 67/00
[52] U.S. Cl. ........................ 560/190; 560/202
[58] Field of Search ................. 560/190, 202

[56] References Cited
U.S. PATENT DOCUMENTS

| | | | |
|---|---|---|---|
| 2,396,626 | 3/1946 | Wiest et al. | 260/464 |
| 4,595,717 | 6/1986 | Patzschke et al. | 523/414 |
| 5,219,958 | 6/1993 | Noomen et al. | 525/10 |

OTHER PUBLICATIONS

Tsushima et al., *Tetrahedron*, 44(17), pp. 5375–5387 (1988).
Quast et al., *Liebigs. Ann. Chem.*, pp. 1305–1308 (1991).

*Primary Examiner*—José G. Dees
*Assistant Examiner*—Barbara S. Frazier
*Attorney, Agent, or Firm*—Richard J. Hammond

[57] ABSTRACT

Dialkyl malonate/alkyl acrylate Michael addition product mixtures having at least three acceptor moieties in a substantial number of the molecules can be consistently prepared without the need for long reaction times or the use of a large excess of the acceptor when the reaction is effected by gradually adding one molar proportion of a dialkyl malonate to at least three molar proportions of an alkyl acrylate which has been preheated to 60°–80° C. in admixture with an initiator and a phase transfer catalyst. In a preferred embodiment, the preheated mixture is maintained at 60°–80° C. for at least one hour before the dialkyl malonate is added in order to increase the percentage of product composed of the heavier components.

18 Claims, No Drawings

PROCESS FOR PREPARING MICHAEL ADDITION PRODUCTS

FIELD OF INVENTION

This invention relates to a process for preparing Michael addition products, and more particularly to such a process permitting better control of the reaction.

BACKGROUND

As disclosed in copending applications Ser. No. 07/947,628 (Sabahi), Ser. No. 07/947,629 (Sabahi et al.-I), and Ser. No. 07/986,204 (Sabahi et al.-II):

(1) useful Michael addition products containing at least one, and preferably more than one, acceptor moiety per molecule can be prepared by reacting a dialkyl malonate with an alkyl acrylate in the presence of an initiator and a phase transfer catalyst, and (2) it was believed that making the Michael acceptor, i.e., the acrylate, the last of the ingredients to be charged to the reaction vessel permitted better control of the reaction temperature and, therefore, improved direction of the reaction to the formation of a desired product.

Sabahi and Sabahi et al. show that the above-described process is capable of providing Michael addition products containing more than one acceptor moiety per molecule. As demonstrated in their working examples, however, the process requires the use of a considerable stoichiometric excess of the acceptor to provide any substantial number of molecules containing at least three acceptor moieties. Moreover, this process employing the large excess of acceptor suffers from long reaction times and lack of reproducibility, and the product compositions are ill defined.

SUMMARY OF INVENTION

It has now been found that dialkyl malonate/alkyl acrylate Michael addition product mixtures having at least three acceptor moieties in a substantial number of the molecules can be consistently prepared without the need for long reaction times or the use of a large excess of the acceptor. This improved process is effected by gradually adding one molar proportion of a dialkyl malonate to at least three molar proportions of a mixture of an alkyl acrylate, an initiator, and a phase transfer catalyst at 60°–80° C.

DETAILED DESCRIPTION

The dialkyl malonate employed as a donor in the novel Michael reaction process may be a single dialkyl malonate or a mixture of such malonates, and the alkyl acrylate utilized as an acceptor may consist of one or more alkyl acrylates.

Dialkyl malonates and alkyl acrylates which are most useful in the practice of the invention are those in which the alkyl groups contain 1–10 carbons. The alkyl groups in such compounds are preferably true alkyl groups (i.e., saturated aliphatic hydrocarbyl groups), such as methyl, ethyl, propyl, isopropyl, butyl, isobutyl, t-butyl, pentyl, hexyl, heptyl, octyl, 2-ethylhexyl, nonyl, and decyl groups, more preferably methyl, ethyl, butyl, hexyl, and/or ethylhexyl groups. However, they may also be groups which are predominantly alkyl in nature, i.e., contain one or more atoms other than the carbon and hydrogen of the alkyl groups as hetero atoms (e.g., oxygen, sulfur, or phosphorus atoms) which are part of the chain or as substituent groups (e.g., alkoxy, halo, or cyano groups) but contain so few of the other atoms that the predominantly hydrocarbyl nature of the groups is preserved.

To preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the alkyl groups to which they most closely correspond, so the term alkyl, as used herein, should be understood as including the predominantly alkyl groups as well as the alkyl groups normally denoted by those terms. Exemplary of such groups are chlorohexyl, bromodecyl, ethoxyoctyl, and cyanononyl.

As already indicated, the reactants are employed in amounts such as to provide an alkyl acrylate/dialkyl malonate mol ratio of at least 3/1; and this mol ratio is preferably in the range of 3-5/1. As the mol ratio is increased, the percentage of product molecules containing the larger number of acceptor moieties is also increased. However, since this percentage is not appreciably increased at mol ratios >5/1, there may be no significant advantage to using more than five mols of acrylate per mol of malonate.

The initiator and phase transfer catalyst used in the process may be any of the initiators and phase transfer catalysts of Sabahi, the teachings of which are incorporated herein by reference. Thus:

(1) the initiator is a base such as an alkali or alkaline earth metal hydroxide, alkoxide, amide, or carbonate, preferably a sodium or potassium hydroxide, alkoxide, amide, or carbonate, and most preferably sodium or potassium carbonate, (2) the amount of initiator is ordinarily ~1–50%, preferably 3–30%, and most preferably 5–10%, based on the weight of the dialkyl malonate, (3) the phase transfer catalyst is preferably an alkylammonium salt such as the tetraalkylammonium chlorides, bromides, fluorides, iodides, sulfates, hydrogen sulfates, carbonates, and phosphates in which the alkyl groups contain 1–20 carbons, and (4) the amount of phase transfer catalyst is typically 0.1–1 mol/mol of dialkyl malonate.

In the process of the invention, the alkyl acrylate is preheated to 60°–80° C. in admixture with the initiator and phase transfer catalyst before the dialkyl malonate is gradually added thereto; and the preheated mixture is preferably maintained at 60°–80° C. for at least one hour prior to the addition of the malonate. The preferred preheating time is one hour, since one hour of preheating is adequate to increase the percentage of product composed of the heavier components, and longer preheating times do not appear to give any significant improvements.

As the dialkyl malonate is added to the preheated alkyl acrylate, it reacts therewith in the presence of the initiator and phase transfer catalyst to form a Michael addition product mixture having at least three acceptor moieties in a substantial number of the molecules—the reaction being complete at the end of the addition. The exothermic reaction is controlled, and the process is reproducible in the preparation of compositions containing a consistent amount of the heavier components, i.e., the molecules containing at least three acceptor moieties. For example:

(1) when methyl acrylate is reacted with dimethyl malonate in the process, the product consistently contains ~25-30% pentamethyl ester of 1,3,3,5,7-heptanepentacarboxylic acid and 10-20% hexamethyl ester of 1,3,3,5,7,9-nonanehexacarboxylic acid and/or 1,3,5,5,7,9-nonanehexacarboxylic acid, and (2) when butyl acrylate is reacted with dimethyl malonate, the final product consistently contains ~20-25% tributyl dimethyl ester of 1,3,3,5,7-heptanepentacarboxylic acid and 5-7% heavier components.

As in Sabahi/Sabahi et al., the process is of particular value in preparing oils for use as lubricants in refrigeration compositions containing fluorohydrocarbons, such as R-134a, as the refrigerants—these lubricants being either oils prepared directly by the Michael reaction or oils obtained by subjecting the Michael products to transesterification reactions.

The following examples are given to illustrate the invention and are not intended as a limitation thereof. In these examples, chemical names of product components are abbreviated as shown below.

| Abbreviation | Full Chemical Name |
| --- | --- |
| tetramethyl ester | tetramethyl ester of 1,3,3,5-pentanetetracarboxylic acid |
| pentamethyl ester | pentamethyl ester of 1,3,3,5,7-heptanepentacarboxylic acid |
| hexamethyl ester | hexamethyl ester of 1,3,5,5,7,9-nonanehexacarboxylic acid and/or 1,3,3,5,7,9-nonanehexacarboxylic acid |
| higher esters | methyl esters of homologs of the above polycarboxylic acids containing >7 carboxy groups |

EXAMPLE 1

Part A

Heat a stirred mixture of 51.6 g (0.6 mol) of methyl acrylate, 2.76 g (0.02 mol) of potassium carbonate, and 0.68 g (0.002 mol) of tetrabutylammonium hydrogen sulfate to 60° C., maintain that temperature for one hour, and then add 26.4 g (0.2 mol) of dimethyl malonate dropwise and under nitrogen over 1.5 hours. A mild exotherm causes the temperature to reach 92° C. during the reaction, which is complete at the end of the addition. GC analysis shows the product to contain 55% tetramethyl ester, 26% pentamethyl ester, 10% hexamethyl ester, and 9% higher esters.

Part B (Comparative)

Repeat Part A except for heating the initial mixture to 50° C. instead of 60° C., beginning the addition of dimethyl malonate upon reaching 50° C., and adding the dimethyl malonate over one hour. A mild exotherm causes the temperature to reach 103° C. during the addition. GC analysis of the reaction mixture at the end of the addition shows the product to contain 60% tetramethyl ester, 25% pentamethyl ester, 8% hexamethyl ester, and 7% higher esters.

EXAMPLE 2

Part A

Repeat Example 1, Part A, except for increasing the amount of methyl acrylate to 86 g (1.0 mol) and adding the dimethyl malonate over 1.3 hours. GC analysis shows the product to contain 44% tetramethyl ester, 30% pentamethyl ester, 15% hexamethyl ester, and 10% higher esters.

Part B

Repeat Part A except for heating the initial mixture to 70° C. instead of 60° C. and maintaining that temperature for two hours before beginning the addition of the dimethyl malonate. GC analysis shows the product to contain 40% tetramethyl ester, 29% pentamethyl ester, 17% hexamethyl ester, and 10% higher esters.

Part C (Comparative)

Repeat Part A except for heating the initial mixture to 50° C. instead of 60° C., beginning the addition of dimethyl malonate upon reaching 50° C., and adding the dimethyl malonate over one hour. GC analysis shows the product to contain 60% tetramethyl ester, 29% pentamethyl ester, and 10% hexamethyl ester.

EXAMPLE 3

Part A

Heat a stirred mixture of 430 g (5.0 mols) of methyl acrylate, 13.3 g (0.1 mol) of potassium carbonate, and 3.4 g (0.01 mol) of tetrabutylammonium hydrogen sulfate under nitrogen to 70° C., maintain that temperature for two hours, and then add 132 g (1.0 mol) of dimethyl malonate over three hours. A mild exotherm causes the temperature to reach a maximum of 85° C. during the reaction; and GC analysis of the product shows it to contain 41% tetramethyl ester, 31% pentamethyl ester, 16% hexamethyl ester, and 7% higher esters.

Part B

Add 745 mL (6.0 mols) of hexanol to the product of Part A, heat for three hours, and collect the overhead light components. Then cool the reaction mixture to room temperature, add heptane and water, separate the aqueous layer, and wash the organic phase with water until neutral. After removal of the heptane and lighter components, the product is an oil having a viscosity of 27.2 $mm^2 \cdot S^{-1}$ at 40° C., a viscosity of 5.1 $mm^2 \cdot S^{-1}$ at 100° C., a viscosity index of 120, and miscibility with R-134a down to −15° C.

What is claimed is:

1. In a process for reacting one molar proportion of a dialkyl malonate with at least three molar proportions of an alkyl acrylate in the presence of a basic initiator and a phase transfer catalyst to prepare a Michael addition product mixture that contains molecules having at least three alkyl acrylate moieties, the improvement which comprises preheating a mixture of the alkyl acrylate, the initiator, and the phase transfer catalyst to 60°-80° C. and then gradually adding the dialkyl malonate to the preheated mixture to effect reaction with the alkyl acrylate.

2. The process of claim 1 wherein the preheated mixture is maintained at 60°-80° C. for at least one hour before the dialkyl malonate is added thereto.

3. The process of claim 2 wherein the preheated mixture is maintained at 60°-80° C. for one hour before the dialkyl malonate is added thereto.

4. The process of claim 1 wherein the alkyl groups of the dialkyl malonate and alkyl acrylate contain 1-10 carbons.

5. The process of claim 4 wherein the dialkyl malonate is dimethyl malonate.

6. The process of claim 5 wherein the alkyl acrylate is methyl acrylate.

7. The process of claim 5 wherein the alkyl acrylate is butyl acrylate.

8. The process of claim 4 wherein the dialkyl malonate is diethyl malonate.

9. The process of claim 8 wherein the alkyl acrylate is methyl acrylate.

10. The process of claim 8 wherein the alkyl acrylate is butyl acrylate.

11. The process of claim 1 wherein one molar proportion of the dialkyl malonate is added to a preheated mixture containing 3–5 molar proportions of the alkyl acrylate.

12. The process of claim 11 wherein the alkyl groups of the dialkyl malonate and alkyl acrylate contain 1–10 carbons and the preheated mixture is maintained at 60°–80° C. for one hour before the dialkyl malonate is added thereto.

13. The process of claim 12 wherein the dialkyl malonate is dimethyl malonate.

14. The process of claim 13 wherein the alkyl acrylate is methyl acrylate.

15. The process of claim 13 wherein the alkyl acrylate is butyl acrylate.

16. The process of claim 12 wherein the dialkyl malonate is diethyl malonate.

17. The process of claim 16 wherein the alkyl acrylate is methyl acrylate.

18. The process of claim 16 wherein the alkyl acrylate is butyl acrylate.

* * * * *